| United States Patent [19] | [11] Patent Number: 4,742,045 |
| Verma et al. | [45] Date of Patent: May 3, 1988 |

[54] GLYCOPEPTIDE ANTIBIOTICS

[75] Inventors: Ashok K. Verma; Anil K. Goel; V. Arjuna Rao; Akella Venkateswarlu, all of Bangalore, India; Robert D. Sitrin, Lafayette Hill, Pa.

[73] Assignee: SmithKline Beckman Corporation, Philadelphia, Pa.

[21] Appl. No.: 891,931

[22] Filed: Jul. 30, 1986

[51] Int. Cl.$^4$ .................... A61K 37/00; C07K 9/00; A23K 1/00
[52] U.S. Cl. .......................... 514/8; 514/9; 530/317; 530/322; 426/635
[58] Field of Search .................... 530/317, 322; 514/8, 514/9; 426/635

[56] References Cited

U.S. PATENT DOCUMENTS

| 4,083,964 | 4/1978 | Michel et al. | 424/118 |
| 4,456,593 | 6/1984 | Herrin et al. | 530/317 |
| 4,462,942 | 7/1984 | Hamill et al. | 530/317 |
| 4,537,715 | 8/1985 | Boeck et al. | 530/322 |
| 4,537,770 | 8/1985 | Michel et al. | 424/118 |
| 4,548,974 | 10/1985 | Bowie et al. | 424/118 |

OTHER PUBLICATIONS

Williams et al., Topics in Antibiotic Chemistry, vol. 5, pp. 119–158 (1980).
Malabarba et al., J. of Antibiotics, vol. 37, No. 9, pp. 988–999.
Barna et al., J. of Antibiotics, vol. 37, No. 10, pp. 1204–1208.
Jeffs et al., J. Org. Chem. vol. 50 pp. 1726–1731.

Primary Examiner—John Kight
Assistant Examiner—Christina Chan
Attorney, Agent, or Firm—Linda E. Hall; Janice E. Williams; Alan D. Lourie

[57] ABSTRACT

Novel glycopeptide antibiotics of the CWI-785 complex are produced by the Actinomycete SKF-CWI-785.

36 Claims, No Drawings

GLYCOPEPTIDE ANTIBIOTICS

FIELD OF THE INVENTION

This invention relates to the field of natural products pharmacology and, more specifically, to a novel glycopeptide compound and hydrolysis products thereof which have antibacterial activity and can be used to enhance the efficiency of animal feed utilization.

BACKGROUND OF THE INVENTION

The glycopeptide, or vancomycin, class of antibiotics are crystalline, amphoteric, strongly laevorotatory compounds of relatively high molecular weight. Structurally, they comprise a polypeptide core aglycone structure having phenolic amino acids and one or more peripheral carbohydrate moieties. See, Williams et al., Topics in Antibiotic Chemistry, Volume 5, pages 119-158. Known members of this class include vancomycin (McCormick et al., U.S. Pat. No. 3,067,099), ristocetin (Philip et al., U.S. Pat. No. 2,990,329), A35512 (Michel et al., U.S. Pat. No. 4,083,964), avoparcin (Kunstmann et al., U.S. Pat. No. 3,338,786) teicoplanin (Bardone et al., J. Antibiot., Volume 31, page 170, 1978), actaplanin (Raun, U.S. Pat. No. 3,816,618), AAD-216 (Bowie et al., EP-A No. 132118), A477 (Raun et al., U.S. Pat. No. 3,928,571), OA7633 (Nishida et al., U.S. Pat. No. 4,378,348), AM 374 (Kunstmann et al., U.S. Pat. No. 3,803,306), K288 (J. Antibiotics, Series A, Volume 14, page 141 (1961), also known as actinoidin).

The glycopeptide antibiotics exhibit antibacterial activity, some having therapeutic uses against gram-positive organisms. In addition, many have been demonstrated to increase animal feed utilization efficiency and, therefore, to be useful to promote animal growth, to improve milk production in ruminants and to treat and to prevent ketosis in ruminants. For example, Reynolds et al., GB No. 2137087A, disclose use of avoparcin to improve milk production; Raun et al., U.S. Pat. No. 3,928,571 disclose use of actaplanin, avoparcin (A477), vancomycin and ristocetin to promote growth and to prevent and to treat ketosis; Hamill et al., U.S. Pat. No. 3,952,095, disclose use of actaplanin to promote growth; and Ingle et al., U.S. Pat. No. 4,206,203 disclose use of avoparcin to prevent and to treat ketosis.

SUMMARY OF THE INVENTION

In one aspect, the invention is a novel glycopeptide complex herein identified as CWI-785. In other aspects, the invention is the individual components of the complex, as represented by the components A, B and C, and hydrolysis products of the complex and its components.

In yet other aspects, the invention is a process for preparing the antibiotics of the invention, an antibacterial composition, a method for treating or preventing infection in an animal by a gram-positive bacteria, an animal feed composition to increase propionate production in the rumen or cecum of a meat or milk producing animal, an animal feed premix, a method of improving the growth rate of a meat producing animal, a method of improving the efficiency of feed utilization in a meat or milk producing animal and a method for improving milk production in a lactating ruminant.

The invention is also a novel actinomycete organism which produces the CWI-785 complex, herein designated SK&F-CWI-785, a representative strain of which was deposited under the terms of the Budapest Treaty in the American Type Culture Collection under accession number ATCC 53296.

These and other aspects described herein below are considered embodiment of the same invention and are fully disclosed herein.

DETAILED DESCRIPTION OF THE INVENTION

The CWI-785 complex can be produced by cultivating a strain of SK&F-CWI-785 having the characteristics of ATCC 53296 or an active mutant or derivative thereof, obtained by procedures known to the art, under submerged aerobic conditions in an aqueous nutrient medium. The organism is grown in a nutrient medium containing an assimilable carbon source, for example an assimilable carbohydrate. Examples of suitable carbon sources include sucrose, lactose, maltose, mannose, fructose, glucose, and soluble starch. The nutrient medium should also contain an assimilable nitrogen source such as fish meal, peptone, soybean flour, peanut meal, cotton seed meal or corn steep liquor. Nutrient inorganic salts can also be incorporated in the medium. Such salts may comprise any of the usual salts capable of providing sodium, potassium, ammonium, calcium, phosphate, sulfate, chloride, bromide, nitrate, carbonate or like ions.

Production of the CWI-785 complex can be effected at any temperature conducive to satisfactory growth of the organism, e.g., about 15°-about 42° C., and is conveniently carried out at a temperature of about 25° to about 28° C.

The medium normally is neutral, but the exact pH can be varied between 5.0 and 9.0 depending on the particular medium used.

The fermentation may be carried out in Erlenmeyer flasks or in laboratory or industrial fermentors of various capacities. When tank fermentation is to be used, it is desirable to produce a vegetative inoculum in a nutrient broth by inoculating a small volume of the culture medium with the vegetative cells of the organism. After obtaining an inoculum in this manner, it is transferred aseptically to the fermentation tank medium for large scale production of the antibiotics. The medium used for the vegetative inoculum can be the same as that employed for larger fermentations, although other media can be employed.

As is customary in aerobic submerged culture processes, sterile air is sparged through the culture medium. Agitation may be maintained by means of agitators generally familiar to those in the fermentation industry.

In general, optimum production of the complex is achieved after incubation periods of about 48-to about 96 hours in stir-jar fermentors or tank fermentors. The course of the fermentation can be followed by analytical HPLC or bioassay.

The CWI-785 complex refers to the mixture of the individual CWI-785 components. As is readily understood by those familiar with natural products fermentation processes, the relative amounts of the individual components, or antibiotics, and their presence in the complex will vary depending on the fermentation conditions, including the duration of fermentation. The CWI-785 complex can be recovered from the fermentation medium by clarifying the whole fermentation broth, such as by filtration, to prepare a mycelial free broth and isolating the complex therefrom by standard techniques. These include, for example, the techniques for isolating various glycopeptides disclosed by Raun et al., U.S. Pat. No. 3,928,571; Nishida et al., U.S. Pat. No. 4,377,348; Hamill et al., U.S. Pat. No. 3,952,095; McCormick et al., U.S. Pat. No. 4,440,753, Hershberger et al., U.S. Pat. No. 4,461,723; and Chan et al., U.S. Pat. No. 4,521,335.

Typically, the complex is isolated from a broth-filtrate by affinity chromatography such as disclosed by Sitrin et al., EP-A-132,117 and by Cassani et al., EP-A-122,969. The eluate can be lyophilized to yield the complex. By way of further example, the broth-filtrate can be processed on a XAD-7 resin and the eluate can be lyophilized or further purified by affinity chromatography prior to lyophilization. The individual components of CWI-785 can be separated from the complex such as by HPLC.

The isolated, lyophilized complex, like other known glycopeptide antibiotics, is a white powder, amphoteric, and laevo-rotatory ($[\alpha]^{20} = -99.1°$ in water). It has a melting point of >300° C. The complex also shares the structural features characteristic of glycopeptides. Specifically, it comprises a core oligopeptide aglycone structure having phenolic amino acids and peripheral carbohydrate moieties. Unlike other known glycopeptides, one of the amino acids in the core aglycone is methionine. The complex displays a typical UV absorption maximum at 280 nm ($E_{1\%}$ about 42) under neutral conditions and at 300 nm ($E_{1\%}$ about 40) under basic conditions. Its pI is 7.90.

The complex comprises several components, including three relatively abundant components. These major components are Factor A, which in a typical formentation and isolation procedure comprises 1–10%, by weight, of the complex; Factor B, 70–80%; and Factor C, 15–30%.

CWI-785b was distinguished from vancomycin, A35512B, actaplanin, actinoidin, LLAM374 and ristocetin by retention time in HPLC. In one HPLC system, CWI-785B co-eluted with the B component of avoparcin. However, FAB-MS data indicated that CWI-785B has a molecular weight of 1760 (peaks at 1761 (M+H), 1783 (M+Na) and 1799 (M+K) whereas the A and B components of avoparcin display peaks corresponding to molecular weights of 1907 and 1941, respectively.

Factor B has an approximate elemental composition of 50.59% carbon, 5.69% hydrogen, 5.95% nitrogen, 2.40% chlorine, 2% sulfur, 0.05% ash and 4.4% weight loss. It has tentatively been assigned the following structure (Formula I):

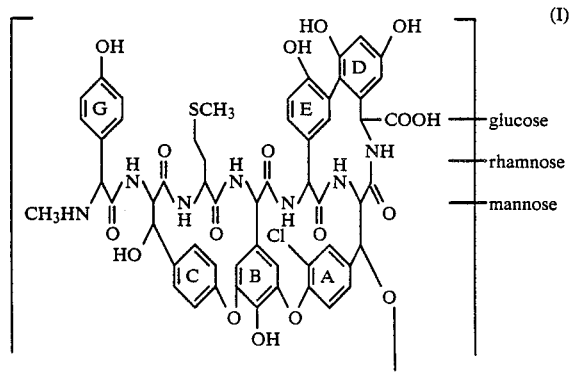

-continued

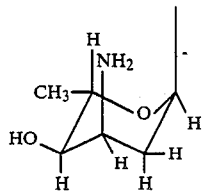

Upon mild hydrolysis (1N HCl, 0.5 h, 110° C.), Factor·B and Factor C are converted to a hydrolysis product herein referred to as HPB4, as well as other hydrolysis products. HPB4 is a pseudoaglycone. It has a molecular weight of 1290 and differs structurally from Factor B in that the only carbohydrate moiety present in HPB4 is ristosamine. A hydrochloride salt preparation (mono-/di-) of HPB4 has an approximate elemental composition of 47.75% carbon, 5.29% hydrogen, 7.40% nitrogen, 1.69% sulfur, 5.76% chlorine and 11.75% weight loss. Following is a numerical listing of $^{13}C$ peaks in HPB4 spectra obtained on 21 mg dissolved in 0.5 ml $D_2O$:DMSO-$d_6$ (1:5 V/V) at an observation frequency of 125.65 MHz:

| | | |
|---|---|---|
| 174.41 | 129.45 | 69.04 |
| 172.88 | 128.08 | 67.49 |
| 170.79 | 127.99 | 64.29 |
| 169.56 | 127.10 | 60.43 |
| 169.37 | 125.99 | 60.36 |
| 167.48 | 125.27 | 59.92 |
| 157.08 | 123.79 | 54.32 |
| 156.64 | 123.46 | 53.68 |
| 155.99 | 123.00 | 48.43 |
| 155.51 | 122.87 | 33.80 |
| 154.91 | 118.23 | 33.38 |
| 150.27 | 117.10 | 31.68 |
| 149.83 | 115.45 | 29.55 |
| 148.25 | 115.29 | 18.80 |
| 139.13 | 108.34 | 14.93 |
| 137.33 | 102.21 | |
| 136.63 | 92.72 | |
| 136.29 | 73.79 | |
| 134.44 | 70.96 | |

HPB4 is the preferred compound of the invention because it is predicted to have an unusually long human half-life (at least about 12 hours) in comparison to vancomycin.

Upon further hydrolysis (1N HCl, 1.5 h., 60°) HPB4 is converted to a hydrolysis product herein referred to as CWI-785B-aglycone. CWI-785B-aglycone has a molecular weight of 1161 and differs structurally from Factor B in that no carbohydrate moieties are present.

Upon mild hydrolysis in oxidizing conditions (5% HCl in DMSO, 0.5 h, 110° C.) Factor B and Factor C are converted to a major hydrolysis product herein referred to as HPB3, as well as other hydrolysis products as described above. The molecular weight of HPB3 is 1306. Thus, HPB3 apparently contains one oxygen atom lacking in HPB4. HPB3 exhibits UV absorption maxima at 280 nm ($E_{1\%}$ about 74, neutral) and at 297 nm ($E_{1\%}$ about 132, basic). When HPB4 is treated with 5% HCl in DMSO (10 mg/ml HPB4, 110° C., 0.5 h), it is oxidized to form HPB3.

Other acid hydrolysis products of Factors B and C include HPB-2M (mannose and ristosamine only), HPB-2G (mannose and glucose only), HPB-2R (mannose and rhamnose only) and the aglycone (no carbohydrates). Isolation and analysis of HPB-2M is described in Example 11, below. The isolation and analysis of the aglycone is described in Example 15, below.

(O)CH$_3$). Thus, Factor A has the structure shown in Formula II:

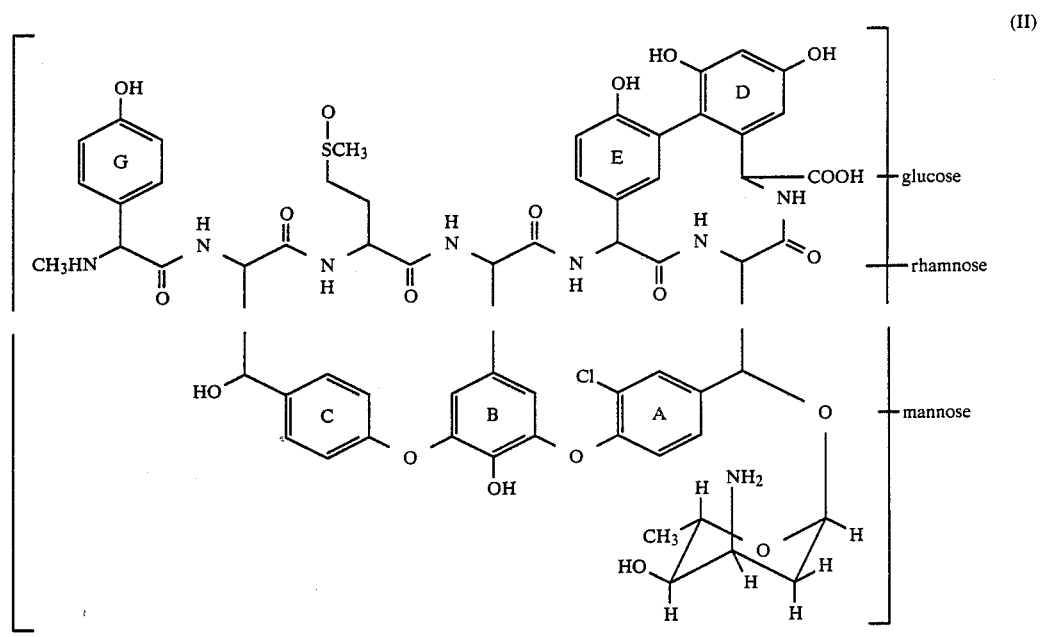

Based on HPLC analysis, the CWI 785B component apparently exists in two isomeric forms, designated B' and B''. Thus, the CWI 785B antibiotic of the invention and the hydrolysis products thereof, include mixtures of the B' and B'' isomers as well as the isolated B' and B'' isomers. The invention includes at least the following four sets of epimers: CWI-785B'/CWI-785B''; HPB4'/HPB4''; HPB3'/HPB3''; and CWI-785B'-aglycone/CWI-785B''-aglycone.

CWI-785B' (free base) isomerizes in solution (water, at 60° for 24 hours) rapidly to CWI-785B'' producing an equilibrium mixture of approximately 75–80% B'' to B'. It is believed that the site of epimerization is at the α-carbon (G-1') of the terminal N-methyl-p-hydroxyphenylglycine (MHPG) residue. Circular dichroism spectral comparison revealed that the MHPG isolated from CWI-785B'' was of the S-configuration while that from the CWT-785B' was of the R-configuration. Isomerization can be prevented by strong-acid protonation of the G-terminal amino group; samples held in pH 3.2 buffered solution at room temperature show little change in the ratio of isomers over a period of several weeks.

In vitro data indicate that CWI-785B' and HPB4' are more active than the corresponding B'' isomers. For example, in vivo data indicate that HPB4' is fourfold more effective than HPB4'' against *S. aureus* 127 and *S. faecalis* 34358. Unless specifically indicated, as used herein, CWI-785B, HPB4 and HPB3 will mean a mixture of epimers. Analogous ' and '' epimers of other components of the CWI-785 complex also exist and are included within the scope of the invention.

Factor A has the same structural characteristics as Factor B, except that its molecular weight is 1776 daltons. Also, the hydrolysis product of Factor A in HCl or in DMSO is HPB3. Thus, Factor A contains the additional oxygen atom in its core aglycone. The additional oxygen atom in Factor A and in HPB3 and other hydrolysis products of Factor A and of Factors B and C (oxidizing conditions) is in the methionine residue (—S-

Factors A' and A'' can be separated by chromatography as described for Factors B' and B''.

Factor C has a molecular weight of 1598 daltons. It differs from Factor B only in that it has only 3 carbohydrate moieties: glucose, rhamnose and ristosamine. Upon mild acid hydrolysis, as described above, Factor C is converted to HPB4. Factors C' and C'' can be separated by chromatography as described for Factors B' and B''.

The CWI-785 components and their hydrolysis products can be converted to physiologically acceptable salts by techniques well-known in the art. Such salts are formed with strong or moderately strong organic or inorganic acids. For example, the complex or individual factor free base is reacted with such acid in an aqueous miscible solvent such as ethanol with isolation of the salt by precipitation such as with excess acetone or in an aqueous immiscible solvent when the acid is soluble therein, such as ethyl ether or chloroform, with the described salt separating directly or by removing the solvent. Exemplary of salts included in this invention are maleate, fumarate, lactate, oxalate, methanesulfonate, ethanesulfonate, benzenesulfonate, tartrate, citrate, salicylate, acetate, propionate, hydrochloride, hydrobromide, sulfate, toluenesulfonic phosphate and nitrate salts.

The CWI-785 antibiotics, which include the CWI-785 complex, each of the CWI-785 components, the hydrolysis products of the complex and of the individual components and salts of all of these, all exhibit antibacterial activity in in vitro and in vivo activity assays against gram-positive organisms and can be used, therefore, to prevent or to treat infection in an animal by, for example, Staphylococcus (including beta-lactam resistant strains), Streptococcus and Clostridium species.

The CWI-785 antibiotics, as defined above, may also be used to make synthetic derivatives which have antibacterial activity such as described by U.S. Pat. No. 4,497,802 and such derivatives are included within the scope of the invention.

Representative results of standard microtiter assays are reported in Tables 1, 2 and 3 which follow, as the minimum inhibitory concentration of antibiotic (μg/ml).

In Table 1, test organisms 1-13 were different strains of *Staphylococcus aureus*, and 14-16 were different strains of *Staphylococcus epidermidis*. In Table 2, test organisms 1-5 were different strains of *S. aureus*; 6, 8, 12 and 14 were different strains of *S. epidermidis*; 7 was a *Staphylococcus haemolyticus*; 9 and 10 were different strains of *Streptococcus faecalis*; 11 was a *Streptococcus pyogenes*; and 13 was a *Staphylococcus saprophyticus*. In Table 3, test organisms 1-3 were different strains of *S. aureus*; 4 and 6 were different strains of *S. epidermidis*; 5 was a *S. haemolyticus* and 7 and 8 were different strains of *Streptococcus faecalis*. Except where individual components are indicated, the CWI-785 antibiotic employed was the CWI-785 complex; in some cases, HCl salts of the CWI-785 antibiotic were employed.

In Table 5 are shown data from standard microtiter assays carried out in a presence of no serum, 50% human serum (hum.) and 50% mouse serum (mse.). The test organisms were 1: *S. aureus*; 2,4 and 5: different strains of *S. epidermidis*; 3: *S. haemolyticus*; 6: *S. saprophyticus*; 7 and 8: different strains of *S. faecalis*. These results show activity in the presence of human and mouse serum.

TABLE 5

| | | MIC (μg/ml) | | | |
|---|---|---|---|---|---|
| Organism | Conditions | Vancomycin | Teicoplanin | HPB3 | HPB4 |
| 1 | No Serum | 1.6 | 3.1 | 0.8 | 1.6 |
| | 50% Hum. Serum | 3.1 | 6.3 | 0.8 | 1.6 |
| | 50% Mse. Serum | 1.6 | 25.0 | 0.8 | 1.6 |
| 2 | No Serum | 1.6 | 12.5 | 0.8 | 1.6 |
| | 50% Hum. Serum | 3.1 | 50.0 | 6.1 | 3.1 |
| | 50% Mse. Serum | 3.1 | 50.0 | 1.6 | 3.1 |
| 3 | No Serum | 3.1 | 12.5 | 1.6 | 1.6 |
| | 50% Hum. Serum | 3.1 | 50.0 | 6.3 | 6.3 |
| | 50% Mse. Serum | 6.3 | 50.0 | 3.1 | 6.3 |
| 4 | No Serum | 1.6 | 12.5 | 0.8 | 3.1 |
| | 50% Hum. Serum | 3.1 | 50.0 | 1.6 | 3.1 |
| | 50% Mse. Serum | 3.1 | 25.0 | 1.6 | 3.1 |
| 5 | No Serum | 1.6 | 12.5 | 0.8 | 0.8 |

TABLE 1

| | Test Organism | | | | | | | | | | | | | | | |
|---|---|---|---|---|---|---|---|---|---|---|---|---|---|---|---|---|
| Antibiotic | 1 | 2 | 3 | 4 | 5 | 6 | 7 | 8 | 9 | 10 | 11 | 12 | 13 | 14 | 15 | 16 |
| Vancomycin | 1.6 | 1.6 | 1.6 | 1.6 | 1.6 | 1.6 | 3.1 | 1.6 | 1.6 | 1.6 | 1.6 | 1.6 | 0.8 | 1.6 | 3.1 | 1.6 |
| Teicoplanin | 1.6 | 1.6 | 3.1 | 1.6 | 1.6 | 1.6 | 3.1 | 6.3 | 6.3 | 3.1 | 3.1 | 0.8 | 1.6 | 12.5 | 6.3 |
| CWI-785 | 12.5 | 12.5 | 25 | 25 | 25 | 12.5 | >25 | 25 | 25 | 25 | 25 | 25 | 12.5 | >25 | >25 | 12.5 |
| CWI-785A | 50 | >50 | >50 | 50 | >50 | 50 | >50 | >50 | >50 | >50 | 50 | >50 | >50 | >50 | >50 | >50 |
| CWI-785B | 25 | 25 | 50 | 50 | 25 | 25 | >50 | 50 | 50 | >50 | >50 | >50 | >50 | >50 | >50 | 25 |
| CWI-785C | 6.3 | 6.3 | 12.5 | 6.3 | 12.5 | 6.3 | 25 | 12.5 | 12.5 | 12.5 | 12.5 | 12.5 | 12.5 | 25 | >50 | 25 |
| Methicillin | 3.1 | 12.5 | 6.3 | 12.5 | 12.5 | 12.5 | >50 | >50 | >50 | >50 | >50 | 50 | >50 | 1.6 | 1.6 | 1.6 |

TABLE 2

| | Test Organisms | | | | | | | | | | | | | |
|---|---|---|---|---|---|---|---|---|---|---|---|---|---|---|
| Antibiotic | 1 | 2 | 3 | 4 | 5 | 6 | 7 | 8 | 9 | 10 | 11 | 12 | 13 | 14 |
| Vancomycin | 1.6 | 1.6 | 1.6 | 1.6 | 1.6 | 1.6 | 3.1 | 1.6 | 1.6 | 1.6 | 0.8 | 1.6 | 1.6 | 1.6 |
| Teicoplanin | 3.1 | 0.8 | 0.4 | 3.1 | 1.6 | 12.5 | 12.5 | 12.5 | <0.1 | <0.1 | 0.2 | 12.5 | 1.6 | 3.1 |
| HPB3 | 0.8 | 0.8 | 0.8 | 0.4 | 0.8 | 0.8 | 1.6 | 0.8 | 0.8 | 0.8 | 0.1 | 0.8 | 0.8 | 0.8 |
| CWI-785B | 25 | 25 | 6.3 | 50 | 25 | 50 | 50 | 50 | 3.1 | 3.1 | 0.2 | 50 | 50 | 25 |
| HPB4 | 1.6 | 0.8 | 0.8 | 0.8 | 0.8 | 1.6 | 1.6 | 3.1 | 0.8 | 0.8 | 0.2 | 1.6 | 1.6 | 0.8 |

TABLE 3

| | | Test Organism | | | | | | | |
|---|---|---|---|---|---|---|---|---|---|
| Antibiotic | Assay Level | 1 | 2 | 3 | 4 | 5 | 6 | 7 | 8 |
| AA2-216-aglycone | 100 g./ml. | 0.4 | 0.4 | 0.8 | 1.6 | 3.1 | 0.8 | 0.8 | 0.8 |
| CWI-785B' | 50 g./ml. | 12.5 | 6.3 | 25.0 | >50 | 50.0 | 50.0 | 1.6 | 1.6 |
| CWI-785B" | " | 25.0 | 12.5 | 50.0 | 50.0 | 50.0 | 50.0 | 3.1 | 1.6 |
| CWI-785B'-aglycone | " | 3.1 | 3.1 | 3.1 | 3.1 | 6.3 | 6.3 | 0.8 | 0.8 |
| CWI-785B"-aglycone | " | 25.0 | 25.0 | 25.0 | 25.0 | 50.0 | 25.0 | 3.1 | 1.6 |

Table 4, which follows, shows MIC data against an expanded panel. The number of strains tested is shown in parentheses below each organism. The average MIC is reported in μg/ml.

TABLE 4

| | Test Organisms | | | | | | | |
|---|---|---|---|---|---|---|---|---|
| Antibiotic | S. aureus (30) | Coag-neg. Staphylococci (24) | Strep. faecalis (12) | Strep. faecalis MBC50 | Group A Strep. (6) | Group B Strep. (4) | Viridans Strep. (2) | JK Diptheroids (19) |
| HPB-4 | | | | | | | | |
| MIC50 | 0.8 | 1.6 | 0.4 | 12.5 | 0.4 | — | — | 0.4 |
| RANGE | (0.2–0.8) | (0.4–3.1) | (0.2–0.8) | (3.1–25) | (0.05–0.8) | (0.1–0.8) | (0.025–0.8) | (0.4–0.8) |
| Vancomycin | | | | | | | | |
| MIC50 | 1.6 | 3.1 | 0.4 | 50 | 0.4 | — | — | 1.6 |
| RANGE | (1.6–6.3) | (0.4–6.3) | (0.4–0.8) | (0.4–>100) | (0.04–0.8) | (0.4–0.8) | (0.05–0.8) | (0.8–1.6) |
| Teicoplanin | | | | | | | | |
| MIC50 | 3.1 | 12.5 | <=0.1 | 6.3 | <=0.025 | — | — | 1.6 |
| RANGE | (1.6–6.3) | (0.8–25) | (<=0.1–0.2) | (1.6–25) | (<0.025–0.4) | (0.1–1.6) | (0.05–0.1) | (0.2–3.1) |

TABLE 5-continued

| Organism | Conditions | MIC (μg/ml) | | | |
|---|---|---|---|---|---|
| | | Vancomycin | Teicoplanin | HPB3 | HPB4 |
| | 50% Hum. Serum | <=0.1 | >100 | 0.8 | 3.1 |
| | 50% Mse. Serum | 3.1 | <=0.1 | 0.8 | 1.6 |
| 6 | No Serum | 1.6 | 1.6 | 0.8 | 0.8 |
| | 50% Hum. Serum | 3.1 | 12.5 | 3.1 | 6.3 |
| | 50% Mse. Serum | 6.3 | 1.6 | 3.1 | 0.2 |
| 7 | No Serum | 1.6 | <=0.1 | 0.8 | 0.4 |
| | 50% Hum. Serum | 3.1 | 6.3 | 3.1 | 3.1 |
| | 50% Mse. Serum | 6.3 | 1.6 | 3.1 | 3.1 |
| 8 | No Serum | 1.6 | <=0.1 | 0.8 | 0.4 |
| | 50% Hum. Serum | 3.1 | 6.3 | 6.3 | 3.1 |
| | 50% Mse. Serum | 6.3 | 3.1 | 3.1 | 3.1 |

The in vivo activity of the CWI-785 complex and its components and hydrolysis products was confirmed by administering selected CWI-785 antibiotics to mice infected with various gram-positive pathogens. In one representative assay, in which mice infected intraperitoneally with 46.8 $LD_{50}$'s of S. aureus (strain 1, Tables 1 and 2) were dosed once, subcutaneously one hour after infection, the following $ED_{50}$'s (mg/kg) were observed: CWI-785B: 2.4, CWI-785C: 3.1, CWI-785: 3.8, HPB3: 0.9, vancomycin: 0.7. In a second representative assay carried out as above except that mice were infected with 3.17 $LD_{50}$'s of S. faecalis (strain 9, Table 2), the following $ED_{50}$'s were observed: HPB3 hydrochloride: 1.6, HPB4 hydrochloride: 1.6, vancomycin: 2.2, teicoplanin: 1.3.

In Table 6, below, is shown the $ED_{50}$ in mg/kg of HPB4 in comparison to vancomycin and teicoplanin. Mice were injected i.p. with the indicated organism and then i.v., 1 hr post infection, with the indicated antibiotic.

Further representative data showing propylactic activity of various compounds of the invention are reported in Tables 7 and 8.

TABLE 6

| | Test Organisms | | | | |
|---|---|---|---|---|---|
| Antibiotic | S. aureus HH 127 (35 × $LD_{50}$) | S. aureus 2620 (24 × $LD_{50}$) | S. epidermidis 2479 (>1000 × $LD_{50}$) | S. haemolyticus 651 (8 × $LD_{50}$) | S. faecalis 34358 (9 × $LD_{50}$) |
| HPB4 | 1.8 | 1.6 | 2.0 | 20 | 1.0 |
| Vancomycin | 0.4 | 1.4 | <1.25 | 10 | 1.3 |
| Teicoplanin | 2.5 | 6.0 | <1.25 | >100 | 1.7 |

TABLE 7

PROPHYLACTIC ACTIVITY OF CWI-785HPB3 AND HPB4 AT 40 mg/kg, 4 hr PREINFECTION vs STAPH. AUREUS HH 127 (S.C.)

| COMPOUND | PERCENT SURVIVAL | $ED_{50}$ |
|---|---|---|
| CWI-785HPB3 (HCl) | 100 | 1.25 |
| CWI-785HPB4 (HCl) | 100 | 1.25 |
| VANCOMYCIN | 20 | 0.31 |

TABLE 8

PROPHYLACTIC ACTIVITY OF CWI-785HPB3 AND HPB4 AT 40 mg/kg (I.V.), 6 hr PREINFECTION vs STAPH. AUREUS HH 127

| COMPOUND | PERCENT SURVIVAL | $ED_{50}$ |
|---|---|---|
| CWI-785HPB3 (HCl) | 60 | <0.156 (90% survival) |
| CWI-785HPB4 (HCl) | 100 | <0.156 (100% survival) |
| AAD-216-AGLYCONE | 100 | 0.50 |
| VANCOMYCIN | 10 | 0.156 |
| TEICOPLANIN | 100 | 0.405 |

The invention includes within its scope pharmaceutical compositions containing at least one of the above-mentioned antibiotic compounds and a pharmaceutically acceptable carrier. The compositions may also contain other active antibacterial agents. The compositions may be made up in any pharmaceutical form appropriate for the route of administration in question. Such compositions are exemplified by solid compositions for oral administration, such as tablets, capsules, pills, powders and granules; liquid compositions for oral administration such as solutions, suspensions, syrups and elixirs; preparations for parenteral administration such as sterile solutions, suspensions or emulsions; and preparations for topical administration such as gels, creams, ointments or salves. Such compositions exhibit, increased solubility. In 40% polyethylene glycol-400 in water (V/V), the solubility of HPB4 free base is about 250 mg/ml. In 40% prophylene glycol in water (V/V), the solubility of HPB4 free base is greater than about 200 mg/ml. Use of such co-solvents does not adversely affect the activity of the antibiotic. The solubility of HPB4.K is about 300 mg/ml. The solubility of HPB4.2HCl is about 600 mg/ml.

For use as an antibacterial agent, the compositions are administered so that the concentration of the active ingredient is greater than the minimum inhibitory concentration for the particular organism treated. The antibiotic compounds of the invention are effective in preventing and treating infection in an animal, including a human, by Gram-positive pathogenic bacteria. A typical parenteral dosage such as by intramuscular injections, for a 70 kg person, is 100 to 2000 mg, preferably 500 to 1000 mg, per day, although the optimum dosage will, of course, depend on factors such as the nature and severity of the bacterial infection, the animal and the route of administration. Optimum dosages can be determined readily by use of standard techniques. Once a day administration is preferred.

The antibiotics of this invention were shown to have activity as animal growth promotants and as animal feed utilization efficiency enhancers. Specifically, CWI-785, CWI-785B, and CWI-785C and monensin (an ionophore antibiotic known to be useful as an animal growth promotant) were dose-titrated in buffered rumen fluid from a donor steer fed a roughage ration. The effects of each additive on 23 hour flask rumen fermentation were assayed. Each flask contained 10 ml of rumen fluid and 10 ml of nutrient broth comprising (mg/flask): casein hydrolysate: 20, maltose: 100, urea: 15, solka floc (cellulose): 400 and starch: 100. The flasks were incubated on a shaker at 39° C. See Table A, below.

TABLE A

| Antibiotic | PPM | ACE | PRO | IBU | BUT | IVA | VAL | TOTAL | % PR |
|---|---|---|---|---|---|---|---|---|---|
| Monensin | 50.00 | 91 | 211 | 104 | 53 | 134 | 38 | 109 | 194 |
|  | 5.00 | 96 | 174 | 77 | 60 | 106 | 41 | 103 | 170 |
|  | 0.50 | 108 | 96 | 101 | 100 | 246 | 114 | 105 | 92 |
| CWI-785 | 50.00 | 92 | 139 | 113 | 96 | 144 | 51 | 104 | 134 |
|  | 5.00 | 95 | 127 | 106 | 93 | 99 | 75 | 102 | 124 |
|  | 0.50 | 104 | 105 | 96 | 104 | 95 | 105 | 104 | 101 |
| CWI-785B | 50.00 | 87 | 135 | 154 | 93 | 149 | 53 | 101 | 133 |
|  | 5.00 | 103 | 133 | 102 | 97 | 106 | 75 | 108 | 124 |
|  | 0.50 | 103 | 102 | 70 | 102 | 100 | 105 | 102 | 100 |
| CWI-785C | 50.00 | 92 | 139 | 163 | 98 | 184 | 49 | 106 | 131 |
|  | 5.00 | 110 | 142 | 56 | 97 | 119 | 61 | 111 | 127 |
|  | 0.50 | 97 | 100 | 93 | 99 | 101 | 97 | 99 | 102 |

Monensin produced shifts in volatile fatty acid (VFA) production consistently with previously observed and reported studies. As can be seen in Table A, CWI-785, CWI-785B and CWI-785C shifted VFA production by increasing propionate but, in several cases, not at a significant expense of acetate and butyrate production. Thus, these compounds are also useful to prevent and treat ketosis in lactating ruminants and to improve milk production in ruminants. In Table A, ACE is acetate, PRO is propionate, IBU is isobutyrate, BUT is butyrate, IVA is isovalerate, VAL is valerate, TOTAL is total VFA and %PR is the amount of propionate relative to TOTAL. Amounts of each VFA are reported as percentages of control ruminant fluid, that is, without additive.

These results show that CWI-785 antibiotics increase propionate production in the rumen and, therefore, can be used to improve efficiency of feed utilization, to promote growth, and to prevent and to treat ketosis. These results also show that CWI-785 antibiotics can increase propionate production without significantly decreasing acetate and butyrate production and, therefore, can be used to improve milk production (increase fat-corrected milk yield) in lactating ruminants. Results of a chick growth study are shown in Table B, below.

TABLE B

| | Dose PPM | # Of Chicks | Weight Day 10 | Weight Day 17 | Feed/Gain 3–10 | Feed/Gain 10–17 | Feed/Gain 3–17 | # of Chicks |
|---|---|---|---|---|---|---|---|---|
| | | | % of Control | | | | | |
| CW1785 | 10.0 | 8 | 101.6 Grams | 108.8 | 98.5 | 84.3 Grams/Gram | 93.2 | 6 |
| Control Rye | 0.0 | 8 | 162.7 | 266.8 | 1.626 | 3.076 | 2.261 | 5 |

8 chicks/rep = 64 chicks/treatment

Results of an in vitro study employing swine intestinal fluid are reported in Table C, below. The swine in vitro model was carried by incubating 1.5 ml of cecum fluid, from a swine fed normal rations, mixed with 1.5 ml of a nutrient broth (3 mg casein hydrolysate, 30 mg maltose, 1.25 mg urea, 0.5 mg lysine, and 30 mg cellobiose) and with up to 166.67 parts per million of a selected growth promotant at 39° C., with oscillation, for about 4–5 hours. Results, percentage of control, are reported in the following table in which all abbreviations are as above and LLAC means L-lactate, ETOH means ethanol and GLU means glucose. The results demonstrate an increase in volatile fatty acids in the cecum which is indicative of improved feed utility efficiency and growth promotion.

TABLE C

| Additive | PPM | ETOH | ACE | PRO | IBU | BUT | IVA | VAL | TOTAL | % PR | GLU | LLAC |
|---|---|---|---|---|---|---|---|---|---|---|---|---|
| | | PERCENT OF CONTROL | | | | | | | | | | |
| Virginiamycin | 166.67 | 0 | 45 | 20 | 0 | 83 | 56 | 84 | 34 | 59 | 151 | 39 |
| | 16.67 | 273 | 58 | 42 | 0 | 95 | 40 | 113 | 52 | 81 | 151 | 32 |
| | 1.67 | 309 | 138 | 147 | 0 | 178 | 251 | 262 | 148 | 99 | 152 | 17 |
| CWI-785 | 16.67 | 397 | 172 | 177 | 0 | 188 | 80 | 259 | 178 | 100 | 150 | 23 |
| | 1.67 | 969 | 132 | 103 | 0 | 114 | 0 | 106 | 114 | 91 | 98 | 97 |
| CWI-785B | 166.67 | 306 | 147 | 157 | 0 | 158 | 137 | 239 | 155 | 101 | 152 | 25 |
| | 16.67 | 377 | 184 | 187 | 0 | 195 | 0 | 256 | 188 | 100 | 152 | 23 |
| | 1.67 | 149 | 103 | 102 | 0 | 105 | 61 | 100 | 102 | 99 | 100 | 101 |
| CWI-785C | 166.67 | 461 | 139 | 158 | 0 | 161 | 148 | 227 | 154 | 103 | 153 | 26 |
| | 16.67 | 220 | 154 | 171 | 0 | 177 | 60 | 256 | 167 | 102 | 153 | 24 |
| | 1.67 | 185 | 108 | 108 | 265 | 109 | 0 | 111 | 108 | 100 | 101 | 101 |

The feed compositions of this invention comprise the normal feed rations of the meat and milk producing animals supplemented by a quantity of an active ingredient selected from among the CWI-785 antibiotics, that is, the complex, its individual components, hydrolysis products of the complex or its components and their salts, or a mixture thereof which is effective for improving the growth rate and feed efficiency of the animals but which is not toxic or noxious to a degree that the animals will reduce ingestion of the ration. The quantity of the active ingredient will vary, as is known to the art, with factors such as the cost of the ingredient, the species and the size of animal, the relative activity of the CWI-785 antibiotic selected or the type of feed ration used as the basal feed.

Representative feed rations for swine and poultry are as follows:

A swine ration for growing hogs of 40–100 pounds body weight is prepared using the following formula:

| | |
|---|---|
| Corn, ground | 78.15% |
| Soybean oil meal, 44% | 17.0% |
| Meat scraps, 50% | 3.0% |
| Oyster shell flavor | 0.4% |
| Bone meal | 0.5% |
| Zinc oxide | 0.01% |
| Vitamin A, B, $B_{12}$ & D supplement | optional |

A chicken ration for broilers is prepared using the following formula:

| | |
|---|---|
| Yellow corn meal | 67.35% |
| Soybean oil meal | 24.00% |
| Menhaden fish meal | 6.00% |
| Steamed bone meal | 1.00% |
| Ground limestone | 1.00% |
| Iodized salt | 0.34% |
| 25% choline chloride | 0.13% |
| Vitamin $B_{12}$ | 0.10% |
| Manganese sulfate | 0.02% |
| Vitamin mix | 0.06% |

Swine feed from weanling to fattening or finishing rations may be supplemented. Swine eat from about 2 lb. of ration per day (for a 25 lb. pig) to 9 lb. per day (for a 150 lb. pig). Most rations are comprised of a corn base supplemented with legume silage, wheat bran, oats, barley, molasses or a protein supplement.

Poultry feeds comprise starter rations, broiler rations and laying rations. The rations are usually based on ground corn, corn meal or soybean meal. The broiler rations, often contain high energy supplements such as added fats, proteins and vitamins. Turkey rations are similar, but comprise only a starting ration and a growing ration. Chickens or pheasants eat from 0.03–0.3 lbs. of feed per day, turkeys twice that much. Estimated intake of feed is dependent on the weight and age of the meat producing animal.

The active ingredients selected from among the CWI-785 antibiotics or a mixture thereof are mixed uniformly with such feed rations to give supplemented rations which are then fed as to custom, which is, most often, ad libitum. Conveniently, to do this, a premix of the supplemental growth promotant of this invention, optionally combined with or without other supplements known to this art such an anthelmintic, a nitrogen source or an antibiotic, for example, virginiamycin or oxytetracycline is prepared by the manufacturer for sale to the formulators or feed lot operators. The concentration of the active ingredients selected from among the CWI-785 antibiotics or a mixture thereof in the premix is usually from 5–75% by weight or a concentration 100–2000 times greater than that in the complete feed ration. The premix form may be liquid or solid. Premix vehicles are corn oil, cottonseed oil, molasses or distillers solubles to form a liquid premix preparation. Sucrose, lactose, corn meal, ground corn, flour, calcium carbonate or soybean meal are often used as bases for solid premix preparations. The premix composition is, then, mixed uniformly with whole ration which is fed to the target animal. Such premix compositions are included in the term "feed compositions" as used herein.

The concentration of the active ingredients selected from among the CWI-785 antibiotics or a mixture thereof in the complete ration is a nontoxic but active quantity chosen, for example, from a range of about 1–1000 parts of active ingredient by weight per million parts of whole feed (ppm) or about 2–115 grams per ton. Advantageously, a nontoxic quantity of active ingredient is chosen from the range of 10–50 ppm.

The method of this invention comprises feeding to monogastric or ruminant, meat or milk producing animals, especially beef and dairy cattle, sheep, swine and poultry, an effective growth promoting but nontoxic quantity of an active ingredient selected from among the CWI-785 antibiotics. Other monogastric animals whose digestive tract also features fermentation in a cecum or cecum-like chamber are rabbits and horses.

The supplemented feed rations, described above, are presented in the animal by methods known to the art. Ad libitum feeding in the pasture, pen or growing shed is most convenient to increase the growth and milking rate of the animal and to increase the feed efficiency of the operation.

The microorganism of the invention was originally isolated from a sample of soil taken from a sandy loam in May, 1979 in Mamnoor, India. The soil sample was processed by heat treatment at 120° C. for 1 h, inoculated into various nutrient media by serial dilution (Waksman's Dilution Technique) and incubated at 28° C. for four weeks. A culture of the original soil isolate, isolated and incubated on a yeast extract malt extract (YME) agar slant for 2 weeks at 28° C., was given the internal accession number 70732. A sample of the organism was deposited in the American Type Culture Collection (ATCC), Rockwell, Md., USA, under accession number 53296.

The isolate is a Gram positive member of the family Actinomycetales. It forms both substrate and aerial mycelia. The substrate mycelium is well-developed, long and branched, showing characteristic curves at terminal portions of the branches during early growth on agar surface. After 60–80 hrs. growth, the curves end up in the formation of interwoven mycelia, giving a mat-like appearance. No bacillary or coccoid structures are formed; in other words, fragmentation of the substrate mycelium is not seen.

Aerial mycelium is none or scanty, showing poor sporulation in most media used (see Table I, below). Aerial mycelia are abundant in Czapek Dox agar and glycerol asparagine agar, only after 3–4 weeks of incubation at 28° C. Moderate aerial mycelia are formed in glucose asparagine agar also, while scanty formation is observed in inorganic salts starch agar. Aerial mycelium monopodially branches with lateral or opposite branches of spore-bearing hyphae (sporophores). In most of the International Streptomyces Project (ISP) media studied, the erect spore-bearing hyphae, often are fused to form a 'synnema' or 'coremia' or, at times, 'knot-like' structures. These are formed by intertwining of sporophores and aerial mycelia. No typical spirals are formed. Aerial mycelium is hygroscopic in a few media.

Sporophores are moderate to poor in most of the media, where aerial mycelia are formed. Sporophores are long, lacking in definite morphology, or sometimes highly flexuous, bearing more than 50 spores, which are linear or elongated; sporophores having 10–50 spores, however, are not uncommon. The spores en masse is light brownish grey to pinkish grey in colour.

The cultural characteristics of Culture No. 70732 (CWI-785) are listed below:

TABLE I

| CULTURAL CHARACTERISTICS OF CWI-785 (CULTURE NO. 70732) | | |
|---|---|---|
| MEDIUM | DETAILS | CHARACTERISTICS OF CWI-785 |
| 1. Yeast extract malt extract | Growth | Good, elevated, colonies small, |
| | Aerial Mycelium | None or very poor |
| | Reverse color | Deep yellowish brown to dark yellowish brown |

TABLE I-continued

CULTURAL CHARACTERISTICS OF CWI-785 (CULTURE NO. 70732)

| MEDIUM | DETAILS | CHARACTERISTICS OF CWI-785 |
|---|---|---|
| | Soluble pigment | Strong yellowish brown |
| Sporophores | | Rarely found, long with no particular morphology, scanty sporulation, 10–50 spores per chain |
| 2. Oat meal agar (ISP) | Growth | Good, small oppressed colonies |
| | Aerial Mycelium | None to very poor |
| | Reverse Color | Dark grayish brown |
| | Soluble Pigment | Nil |
| | Sporophores | Formed rarely, flexuous, more than 50 spores. Large number of 'coremia' encountered. |
| 3. Glycerol asparagine agar (ISP) | Growth | Good, slightly elevated |
| | Aerial Mycelium | Profuse, powdery, grayish pink to pinkish gray |
| | Reverse Color | Dark grayish reddish brown |
| | Soluble Pigment | Moderate pink |
| | Sporophores | Highly flexuous or long chains with no particular morphology, having more than 50 spores, linear; no coils or spirals seen. Large number of 'coremia' present. |
| 4. Inorganic salts starch agar | Growth | Good, colonies elevated |
| | Aerial Mycelium | Scanty, only in the periphery of the colony |
| | Reverse Color | Reddish black |
| | Sporophores | No definite morphology, no typical spirals or hooks or coils present. 10–50 spores per chain; 'coremia' present. |
| 5. Bennett's agar | Growth | Good, irregular colonies, slightly elevated |
| | Aerial Mycelium | None |
| | Reverse Color | Deep yellowish brown |
| | Soluble Pigment | Deep orange yellow |
| | Sporophores | Not formed |
| 6. Tyrosine agar (ISP) | Growth | Moderate, tiny colonies, with shining surface |
| | Aerial Mycelium | None |
| | Reverse Color | Moderate yellowish pink |
| | Soluble Pigment | Nil |
| | Sporophores | Not formed |
| 7. Czapek-Dox agar | Growth | Good, colonies slightly elevated |
| | Aerial Mycelium | Abundant, light gray to pinkish gray |
| | Reverse Color | Dark reddish brown |
| | Soluble Pigment | Brownish orange |
| | Sporophores | Long spore chains, showing no particular morphology; highly flexuous ones are seen rarely. More than 50 spores in each chain. No coils, hooks seen. |
| 8. Glucose asparagine agar | Growth | Good, small, elevated |
| | Aerial Mycelium | Moderate, light brownish gray |
| | Reverse Color | Brownish black |
| | Soluble Pigment | Deep yellowish brown |
| | Sporophores | Long spore chains, highly flexuous sometimes with more than 50 spores in each chain. |
| 9. Glucose yeast extract agar | Growth | Good, colonies irregular, elevated and wrinkled |
| | Aerial Mycelium | None |
| | Reverse Color | Deep yellowish brown |
| | Soluble Pigment | Strong orange |
| | Sporophores | Not seen |
| 10. Nutrient agar | Growth | Poor, tiny, elevated with shining surface |
| | Aerial Mycelium | None |
| | Reverse Color | Light yellowish brown |
| | Soluble Pigment | Light orange yellow |
| | Sporophores | Not seen |
| 11. N-Z amine agar with soluble starch and glucose | Growth | Good, elevated, irregular and wrinkled |
| | Aerial Mycelium | None |
| | Reverse Color | Deep yellowish brown |
| | Soluble Pigment | Strong brown |
| | Sporophores | Not found |
| 12. Potato carrot agar | Growth | Moderate, tiny colonies, with shining surface |
| | Aerial Mycelium | None |
| | Reverse Color | Light orange yellow |
| | Soluble Pigment | Nil |
| | Sporophores | Not found |
| 13. Potato-Dextrose agar | Growth | Good, elevated colonies with wrinkles |
| | Aerial Mycelium | None |
| | Reverse Color | Brownish black |
| | Soluble Pigment | Strong reddish brown |
| | Sporophores | None observed |
| 14. Sabouraud's agar | Growth | Good, elevated, colonies irregular and wrinkled |
| | Aerial Mycelium | None |
| | Reverse Color | Dark yellowish brown to deep yellowish brown |
| | Soluble Pigment | Deep orange |
| | Sporophores | Not formed |
| 15. Streptomyces medium | Growth | Moderate, colonies circular or irregular, elevated with shining surface |
| | Aerial Mycelium | None |

TABLE I-continued

CULTURAL CHARACTERISTICS OF CWI-785 (CULTURE NO. 70732)

| MEDIUM | DETAILS | CHARACTERISTICS OF CWI-785 |
|---|---|---|
| | Reverse Color | Dark brown |
| | Soluble Pigment | Nil |
| | Sporophores | Not found |

Stock cultures of CWI-785 are grown on the above-noted media at 28° C. and observations of growth, aerial mycelium, reverse color, soluble pigment and sporophores were made after a period of 7, 14, 21 and 28 days. Colors indicated were those of the Inter-Society Color Council—National Bureau of Standards (ISCC-NBS) codes (Kelly, K. L., and D. B. Judd, 1976, Color Universal Language, Dictionary of Names. NBS Special Publication 440. US Department of Commerce, National Bureau of Standards, Washington, D.C.)

The biochemical and physiological characteristics of Culture No. 70732 (CWI-785) are as follows.
Growth in different temperatures:
20° C.—Moderate
20° C.-37° C.—Good
55° C.-No growth
No melanoid pigments are formed.
Gelatin is fast liquified.
Litmus milk is acidified.
Tolerates up to 5% concentration of Sodium chloride; shows no growth above 5% level. Grows in acidic as well as alkaline pH (pH 4–pH 10)
Urease positive, starch utilized.
Carbon Utilization:
Utilizes glucose, arabinose, glycerol, rhamnose, fructose, sucrose, galactose, mannitol, salicin, trehalose and xylose; but does not utilize inositol, cellulose, inulin and raffinose.

CHEMOTAXONOMY

Analyses of whole cell hydrolysates indicate the presence of meso-isomer of 2,6-diaminopimelic acid (DAP) and absence of diagnostic sugars, madurose and arabinose. However, galactose and rhamnose are present. Analysis of the pure cell-wall hydrolysates indicates that the cell walls contain alanine, glutamic acid, aspartic acid and other amino acids (Lechevalier, M. P., and H. A. Lechevalier, "The Chemotaxonomy of Actinomycetes," issued at the Actinomycete Taxonomy Workshop, Rice University, Houston, Tex., August 13, 1978).

The major distinguishing characteristics of the above organism are:
(i) conspicuous and copious formation of 'synnema' or 'coremium'
(ii) meso-DAP in its cell wall (Cell Wall Type III), and absence of madurose and arabinose in its whole cell (no characteristic whole cell sugar pattern) and
(iii) its ability to produce novel glycopeptide antibiotics.

EXAMPLES

The following examples are illustrative, and not limiting, of procedures which can be used to produce CWI-785 complex, its components and hydrolysis products of CWI-785 and its components.

EXAMPLE 1

Seed Development

Seed was developed by inoculating one fully-grown slant (slant prepared from lyophilized culture No. 70732) in 90 ml of presterilized CEI-13 (see below) in a 500 ml wide-mouth Erlenmeyer flask. The flask was incubated at 28° C., using a rotary shaker (220–240 rpm/min) for 50–52 h.

Secondary fermentation was done by inoculating the seed (5–7 ml) into 1 L wide-mouth Erlenmeyer flasks, each containing 200 ml of presterilized CEI-44 and CEI-53 (see below). The flasks were incubated at 28° C. using a rotary shaker (220–240 rpm/min) for 48 hours.

The media identified herein as CEI-13, CEI-44 and CEI-53 are as follows:

| | G/L |
|---|---|
| CEI-13 | |
| Starch | 30 |
| Sucrose | 10 |
| Dextrose | 10 |
| Soy Peptone | 15 |
| Corn Steep Liquor (CSL) | 10 |
| $K_2HPO_4$ | 3 |
| NaCl | 1 |
| Mineral Solution | 10 ml |
| $CaCO_3$ | 3 |
| pH - 7.0 | |
| CEI-44 | |
| Starch | 25 |
| Glucose | 7 |
| Glycerol | 5 |
| Soytone | 10 |
| Yeast Extract | 3 |
| $MgSO_4\ 7H_2O$ | 0.5 |
| $MnSO_4\ 2H_2O$ | 0.02 |
| $CaCO_3$ | 2 |
| NaCl | 1.5 |
| CSL | 1.5 |
| pH - 6.8–7.0 | |
| CEI-53 | |
| Starch | 20 |
| Dextrose | 12 |
| Sucrose | 8 |
| Soytone | 5 |
| Cotton Seed Protein Meal | 5 |
| Ammonium Sulfate | 2.5 |
| $MgSO_4\ 7H_2O$ | 0.5 |
| Fish Meal | 2 |
| $CaCO_3$ | 2.5 |
| CSL | 1.5 |
| pH - 6.6 | |

EXAMPLE 2

Isolation and Purification of Complex

Nine L of a broth filtrate (pH 7.10) prepared from recultures of secondary shake-flask cultures substantially as described in Example 1, above, were processed on an XAD-4 resin column (55×750 mm, flow rate: 400 ml/hr). The column was washed with water (pH 7.0) and eluted with 50% aqueous methanol and 100% methanol. The eluates were concentrated using a Buchi rotary evaporator and lyophilized to yield 14.7 g of 50% aqueous methanol product and 1.6 g of 100% methanol product.

The effluent from XAD-4 resin was then processed on XAD-7 resin and elution was again carried out with 50% aqueous methanol and 100% methanol. The eluates were concentrated and lyophilized to yield 4.33 g complex from aqueous methanol eluate and 330 mg complex from methanol eluate.

EXAMPLE 3

Isolation and Purification of Complex—Alternate Procedure

Alternatively, 1.4 liters of broth filtrate prepared from recultures of secondary shake-flask cultures substantially as described in Example 1, above, were processed directly on XAD-7 resin column. The column was washed with water and eluted with 50% aqueous methanol and 100% methanol. The eluates were concentrated on a Buchi rotary evaporator and lyophilized to yield 1.48 g of complex from aqueous methanol eluate and 300 mg of complex from methanol eluate.

EXAMPLE 4

Separation of Components

Lyophilized complex prepared substantially as described in Examples 2 and 3, above, was further purified by affinity chromatography using Affi-Gel®10-D-ala-D-ala. See, Sitrin et al., EP-A No. 132,117.

The affinity purified material was used to standardize HPLC conditions on a semi-preparative column as follows:

| Column: | 10 × 250 mm |
| --- | --- |
| | Ultrasphere ODS 5 μm |
| Mobile phase: | 0.1 M phosphate buffer (pH 3.2) |
| | 10% acetonitrile |
| Flow rate: | 4 ml/min |
| Detection: | 254 nm 0.08 Absorbance Units Full Scale (AUFS) |

The retention time (min) and approximate relative amounts by percent of total of the observed peaks were:

| RT | Amount (%) |
| --- | --- |
| 3.36 | 2.42 |
| 3.73 | 1.67 |
| 4.48 (Factor A) | 3.20 |
| 4.83 | 1.72 |
| 5.86 (Factor B) | 42.38 |
| 7.78 | 12.08 |
| 11.15 | 7.81 |
| 14.61 (Factor C) | 29.02 |

Preparative scale HPLC was then carried out as follows:

| Column: | Whatman M-20 |
| --- | --- |
| | ODS-3 |
| Mobile phase: | 0.1 M phosphate buffer (pH 3.2) |
| | 10.6% acetonitrile |
| Flow rate: | 20 ml/min |
| Detection: | 254 nm |

Three g of complex (affinity purified) were separated. Four fractions were collected. Individual fractions were concentrated on a Buchi rotary evaporator to remove acetonitrile and were processed on a diaion HP-20 resin column. After repeated water wash, the column was eluted with 50% aqueous acetonitrile. The eluent was concentrated and lyophilized to yield the following products.

| Fraction | Weight | % Yield |
| --- | --- | --- |
| 1 | 0.195 g | 6.50 |
| 2 | 1.24 g | 41.30 |
| 3 | 0.083 g | 2.76 |
| 4 | 0.158 g | 5.26 |

Fractions 2 and 4 are Factors B and C, respectively. Fractions 1 and 3 were enriched in other components including, in Fraction 1, Factor A.

EXAMPLE 5

HPLC of Factors A, B & C

Nine g of complex were separated substantially as described above. Fractions containing Factors A, B and C were separately analyzed by HPLC as follows:

| Column: | 4.6 × 150 mm |
| --- | --- |
| | ODS 5 μm |
| Mobile phase: | 0.1 M phosphate buffer (pH 3.2) |
| | 7% acetonitrile for 1 min with |
| | gradient to 34% in 13 min |
| Detection: | UV 280 nm 0.100 AUFS |

Factor A had a retention time of 1.41 min and comprised 75% (460 mg) of the Factor A fraction. Factor B had a retention time of 6.46 and comprised virtually 100% of the Factor B fraction. Factor C had a retention time of 8.19 and comprised virtually 100% of the Factor C fraction.

EXAMPLE 6

Alternate Isolation of Complex

The purified complex antibiotic was also isolated by direct adsorption of the broth-filtrate on a 10-D-ala-D-ala-Affi-Gel® column. For this, 100 ml of broth-filtrate was processed on Affi-Gel® column (10×150 mm, flow rate 60 ml/hr). The column was washed with water and elution was carried out with 30–70% acetonitrile in 0.1M NH$_4$OH. The eluate was concentrated and lyophilized to yield 114 mg of purified complex.

EXAMPLE 7

Hydrolysis Products

CWI-785 complex was hydrolyzed substantially as described by Chan et al., U.S. Pat. No. 4,521,335 which is incorporated herein by reference as though fully set forth, that is, in 5% HCl/DMSO at 100°–110° C. for 15–30 min. The hydrolyzed products were purified on an affinity chromatography column (D-ala-D-ala) substantially as described above, concentrated in vacuum and lyophilized. HPLC was carried out as follows:

| Column: | 10 × 250 mm ODS 5 μm |
| --- | --- |
| Mobile phase: | .01 M phosphate buffer (pH 3.2) |
| | 20% acetonitrile |
| Flow rate: | 2 ml/min |
| Detection | 254 nm 0.08 AUFS |

About 12 peaks were observed. The most abundant hydrolysis product (48.79%), which had a retention time of 30.52 mins, was HPB3. The other peaks, which had lower retention times, were other hydrolysis products.

EXAMPLE 8

HPB3

In a typical hydrolysis experiment, CWI-785B (250 mg) was dissolved in 5 ml of 5% HCl/DMSO solution in a sealed tube. The sealed tube was placed in a boiling water bath for 35 mins, cooled and cracked open. The contents were diluted to 100 ml with water and brought to pH 6.0–7.0 with 6N $NH_4OH$. The hydrolyzed product was then absorbed on the affinity gel and the active material eluted with 0.1N $NH_4OH/CH_3CN$. The eluate was concentrated in vacuum and lyophilized to yield about 200 mg of hydrolyzed complex. The complex comprised as many as 7–8 components, the major component of which (60–75%) was HPB3. One of the minor components was HPB4.

The hydrolyzed complex is then separated on HPLC. The fractions are concentrated to remove $CH_3CN$ and absorbed on XAD-2 resin for desalting. Elution is carried out with 40% aq. $CH_3CN$, the eluate concentrated and lyophilized to give the respective hydrolyzed components.

In order to evaluate whether the major hydrolysis product (HPB3) from component A and C was similar to that of component B, small-scale hydrolysis of components A and C was performed. The major hydrolysis product from each was found to be the same by HPLC analysis and by co-injection with HPB3.

EXAMPLE 9

Preparation of HPB4

CWI-785B (100 mg) was dissolved in 2 ml of 1N HCl in a Pierce reaction tube and heated at 110° C. for 30 min. The reaction mixture was cooled, diluted with water (100 ml) and processed over Diaion HP-20 resin. After water wash, the column was eluted with 50% aqueous acetonitrile. The eluate was concentrated on a Buchi rotary evaporator and lyophilized to yield 63 mg of product.

HPLC of the hydrolyzed product indicates HPB4 was the major component (75–80%). The hydrolyzed complex is then separated on HPLC. Fractions containing HPB4 are concentrated to remove acetonitrile and desalted on HP-20 resin. The elution is carried out with 50% aqueous acetonitrile and the eluate is concentrated and lyophilized to yield pure HPB4.

EXAMPLE 10

Oxidation of HPB4 to HPB3

HPB4 is converted to HPB3 by treatment with 5% HCl in DMSO. For this purpose, HPB4 (5 mg) is treated with 0.2 ml of 5% HCl in DMSO in a Pierce reaction tube for 30 min. at 110° C. The reaction mixture is diluted with water, adsorbed on HP-20 resin and eluted with 50% aqueous acetonitrile. The eluate on HPLC indicates a complete oxidation of HPB4 to HPB3.

EXAMPLE 11

Preparation of HPB-2M

One gram of CWI-785 complex was taken in 25 ml of 0.1N HCl in a round bottom flask with a reflux condenser. The mixture was heated at 90°–100° C. and the reaction products were monitored via HPLC at different time intervals. Reaction was stopped after 2 h, the reaction mixture was diluted with water and adsorbed on HP-20 resin. After water wash, elution was carried out first with 50% aqueous methanol followed by 50% aqueous $CH_3CN$. Aqueous methanol eluted most of the unreacted material, whereas most of the HPB-2M was eluted with aqueous $CH_3CN$; the product (134 mg) was purified by preparative HPLC and the fraction containing HPB-2M was desalted on HP-20 to yield 23 mg of the pure product.

Component 'C', HPB-2M and HPB-4 containing three, two and one sugar moieties respectively, showed the following retention times in analytical HPLC. HPB-3, an oxidized form of HPB-4, is also included for comparison.

| HPLC CONDITIONS (ANALYTICAL) | | |
|---|---|---|
| Column: | 4.6 × 150 mm ultrasphere ODS 5 μm | |
| Mobile Phase: | 0.01 M phosphate buffer pH 3.2 20% acetonitrile | |
| Flow Rate: | 1.5 ml/min | |
| Detection: | 280 nm, 0.1 AUFS | |
| COMPOUNDS | RT (min) | SUGARS PRESENT |
| Component 'C' | 1.77 | Glucose, rhamnose, ristosamine |
| HPB-2M | 5.10 | mannose, ristosamine |
| HPB-4 | 8.95 | ristosamine |
| HPB-3 | 4.46 | ristosamine (and oxygen) |

The in vitro activity profile of HPB-2M was similar to that of HPB-4.

Carbohydrate analysis of HPB-2M was carried out as follows. HPB-2M (5 mg) was taken in 1 ml of 2N HCl in a sealed tube and heated at 100° C. for 2 h. The reaction mixture was diluted with 3 ml of water and passed through Sep-Pak C-18 cartridge. The effluent was collected, lyophilized and dissolved in 0.2 ml of water. Paper chromatography was carried out in n-Butanol:water:Pyridine:Toluene mixture (5:3:3:4) for 48 h. The spots were detected by spraying with analine-phthalate solution and heating at 100° C. The chromatogram showed the presence of mannose in HPB-2M.

EXAMPLE 12

Conversion of HPB-2M to HPB-4

HPB-2M (1 mg) was taken in 0.2 ml of 1N HCl in a sealed tube and heated for 1 h at 100° C. The reaction mixture was diluted to 1 ml with water and analyzed via HPLC. HPLC indicated complete absence of HPB-2M and its conversion to HPB-4.

EXAMPLE 13

Potassium Salts of HPB4

A 600 mg sample of HPB4 free base was suspended in 4 ml of water and to this was added, drop-wise, 1N KOH solution until all the solid dissolves. The potassium salt was precipitated by addition of 4 to 5 volumes of $CH_3CN$. The precipitate was separated by centrifugation, washed with $CH_3CN$, dissolved in $H_2O$ and lyophilized to yield 503 mg of HPB4.K. The product, HPB4.K, is stored in aqueous solution in a stoppered vial at room temperature, as upon exposure to air, the solution tends to become turbid.

In vitro evaluation of the potassium salt, HPB4.K, showed an activity profile similar to that of HPB4.HCl. The solubility of the potassium salt is about 300 mg/ml in water. A 100 mg/ml aqueous solution had a pH of 9.29.

EXAMPLE 14

Hydrochloride Salts of HPB3 and HPB4

Both HPB3 and HPB4 are readily converted to their water soluble hydrochloride salts. For this purpose, 10 mg of HPB3 or HPB4 is suspended in 1 ml of water; the suspension is brought to pH 3 with 0.1N HCl and the resulting solution is lyophilized to yield the respective hydrochloride salts.

The above description and examples are illustrative of the invention and of preferred embodiments thereof. The invention, however, is not limited to the embodiments specifically described herein but rather includes all modifications coming within the scope of the claims which follow.

EXAMPLE 15

Preparation of CWI-785B-aglycone

500 Mg of lyophilized HPB4 in 72 ml of 1.0N HCl was heated at 60° under nitrogen for 1.5 hours. The cooled solution was neutralized with concentrated ammonia. The product was purified on an affinity chromatography column (D-ala-D-ala) substantially as described above, concentrated in vacuum and lyophilized to yield 29 mg. of the CWI-785B-aglycone.

EXAMPLE 16

HPLC Separation of CWI-785B' and CWI-785B"

Factor B, obtained substantially as described in Example 4, was separated into CWI-785B' and CWI-785B" by HPLC using the following conditions:

| Column: | 4.6 × 150 mm ODS 5 μm |
|---|---|
| Mobile phase: | 0.01 M phosphate buffer (pH 3.2) 7% acetonitrile with gradient to 34% in 14 min; 34% acetonitrile for 2 minutes. Flow rate: 1.5 ml/minute. |
| Detection: | uv 220 nm 0.05 AUFS |

CWI-785B' had a retention time of 6.04 minutes; CWI-785B" had a retention time of 6.38 minutes. The starting ratio of B' to B" was approximately 71:29.

The isomers of CWI-785B-aglycone and HPB3 are similarly separated. The retention times are as follows: CWI-785B'-aglycone 11.17 minutes; CWI-785B"-aglycone 11.48 minutes; HPB3' 11.6 minutes; and HPB3" 11.82 minutes.

EXAMPLE 17

HPLC Separation of HPB4' and HPB4"

An 80:20 mixture of CWI-785B":B' which was hydrolyzed into HPB4' and HPB4" by HPLC using the following conditions:

| Column: | 4.6 × 150 nm Octyl 5 μm |
|---|---|
| Mobile phase: | 0.05 M phosphate buffer (pH 6.0); 7% acetonitrile with gradient to 34% in 14 minutes; 34% acetonitrile for 2 minutes. Flow rate: 1.5 ml/minute. |
| Detection: | 220 nm, 0.05 AUFS |

HPB4" had a retention time of 10.76 minutes; HPB4' had a retention time of 11.21 minutes. The amount of HPB4" was approximately two fold greater than the amount of HPB4'.

We claim:

1. The CWI-785 complex of formula (I)

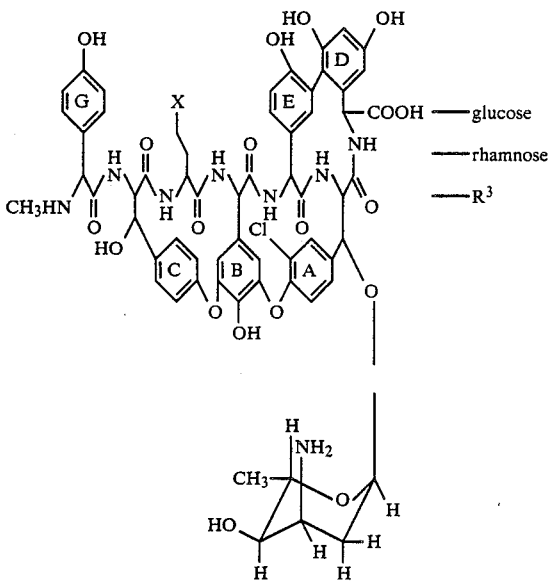

wherein
X is SCH$_3$ or

and

R$^3$ is hydrogen or mannose produced by culturing the Actinomycete SK & F-CWI-785 having the identifying characteristics of ATCC 53296, or an active mutant or derivative thereof, in an aqueous nutrient medium containing assimilable sources of nitrogen and carbon under submerged aerobic conditions.

2. The glycopeptide antibiotic CWI-785B which has the structure:

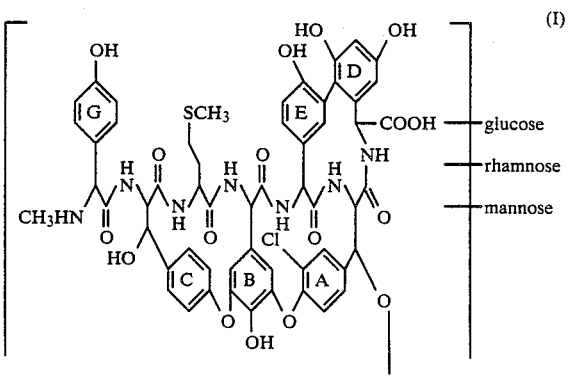

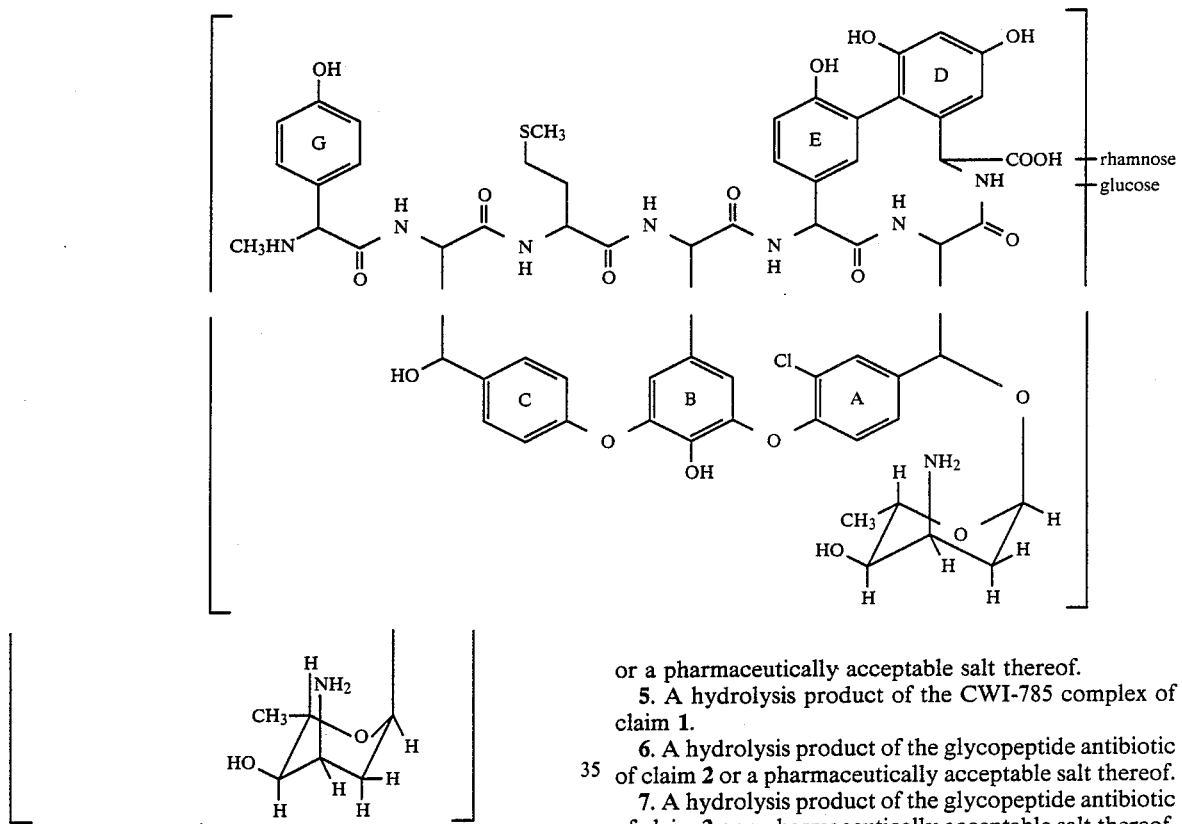

or a pharmaceutically acceptable salt of the antibiotic.

3. The glycopeptide antibiotic CWI-785A which has the structure:

or a pharmaceutically acceptable salt thereof.

4. The glycopeptide antibiotic CWI-785C which has the structure:

or a pharmaceutically acceptable salt thereof.

5. A hydrolysis product of the CWI-785 complex of claim 1.

6. A hydrolysis product of the glycopeptide antibiotic of claim 2 or a pharmaceutically acceptable salt thereof.

7. A hydrolysis product of the glycopeptide antibiotic of claim 3 or a pharmaceutically acceptable salt thereof.

8. A hydrolysis product of the glycopeptide antibiotic of claim 4 or a pharmaceutically acceptable salt thereof.

9. The glycopeptide antibiotic CWI-785 HPB4 which has the structure:

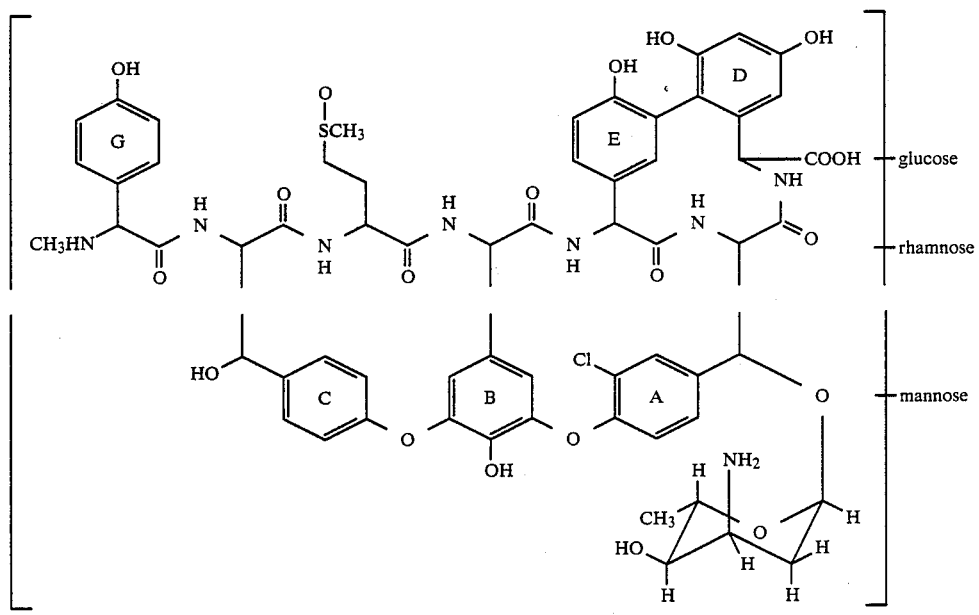

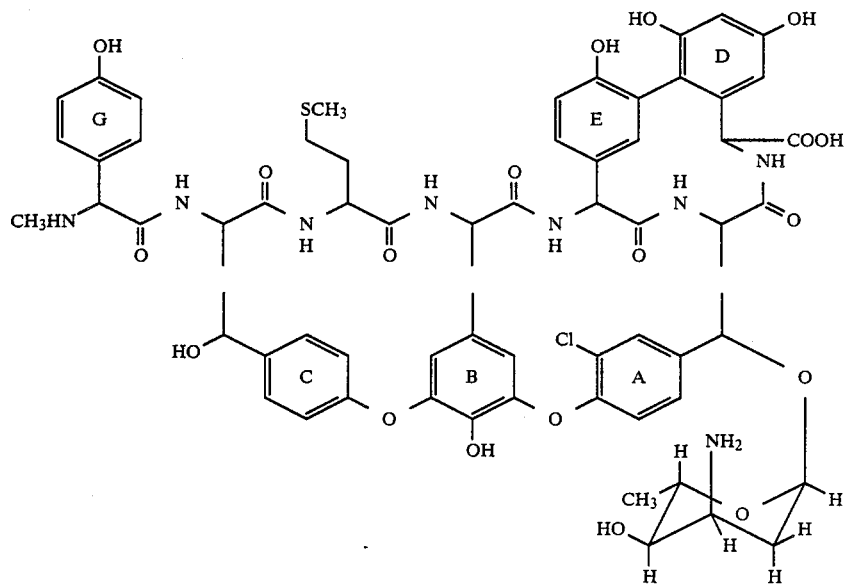
or a pharmaceutically acceptable salt of the antibiotic.
10. The glycopeptide antibiotic CWI-785 HPB3 which has the structure:
or a pharmaceutically acceptable salt of the antibiotic.
11. The glycopeptide antibiotic CWI-785 HPB-2M which has the structure:
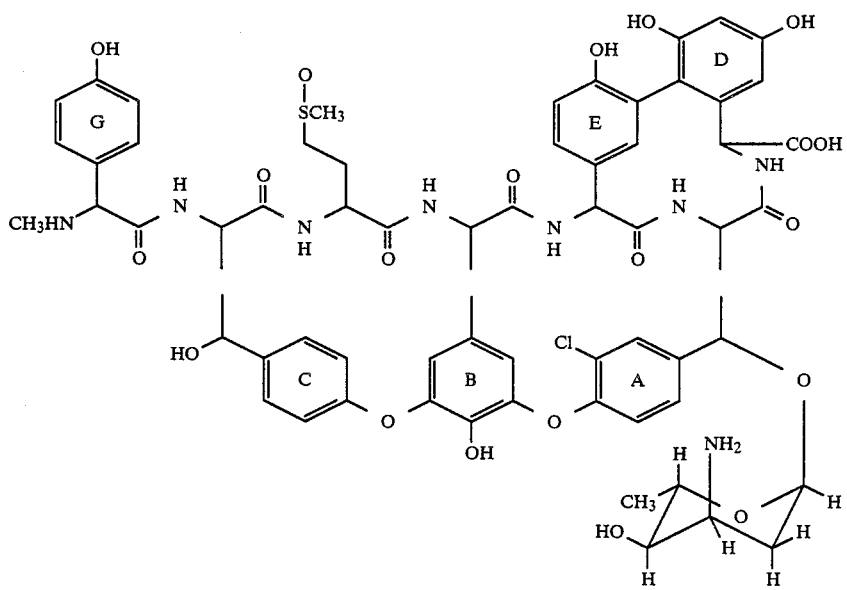
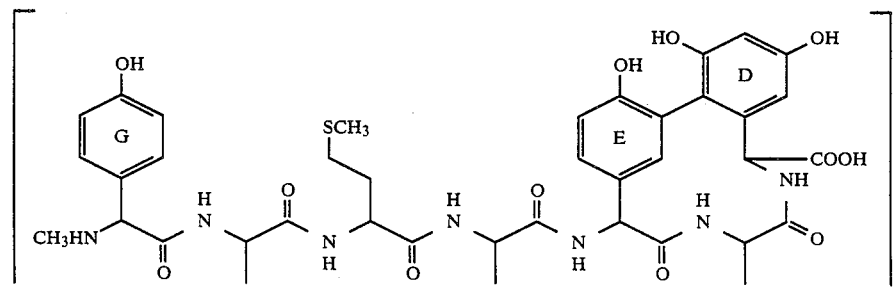

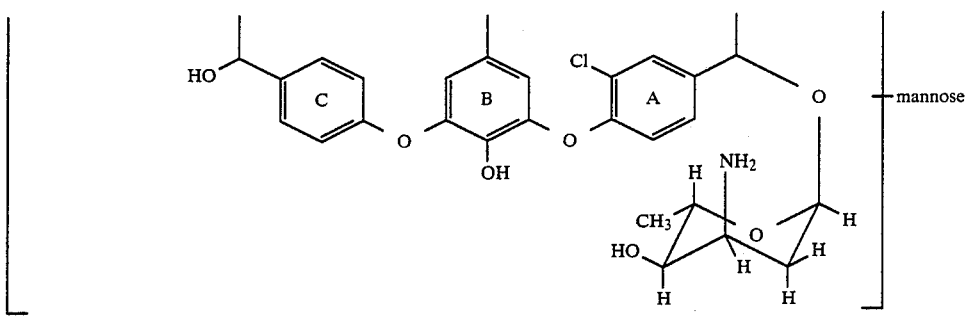

or a pharmaceutically acceptable salt thereof.

12. The antibiotic CWI-785B-aglycone which has the structure:

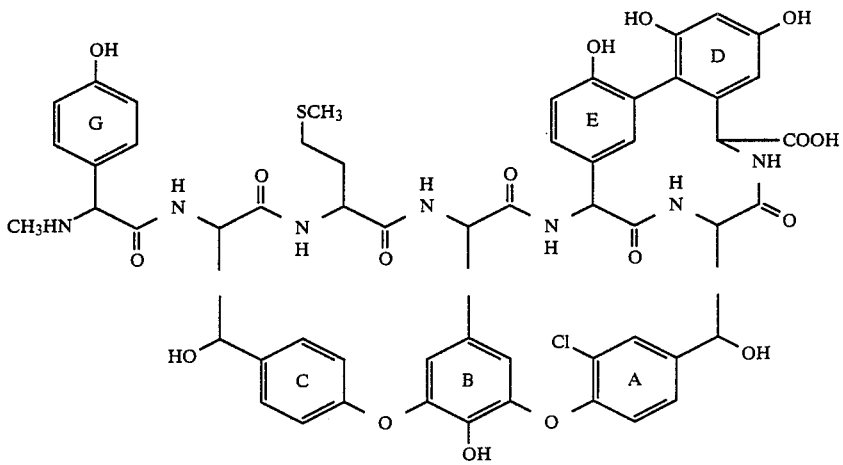

or a pharmaceutically acceptable salt of the antibiotic.

13. An antibacterial composition comprising an antibacterial effective amount of the glycopeptide antibiotic complex of claim 1 and a pharmaceutically acceptable carrier.

14. An antibacterial composition comprising an antibacterial effective amount of the glycopeptide antibiotic of claim 2 and a pharmaceutically acceptable carrier.

15. An antibacterial composition comprising an antibacterial effective amount of the glycopeptide antibiotic of claim 3 and a pharmaceutically acceptable carrier.

16. An antibacterial composition comprising an antibacterial effective amount of the glycopeptide antibiotic of claim 4 and a pharmaceutically acceptable carrier.

17. An antibacterial composition comprising an antibacterial effective amount of the glycopeptide antibiotic of claim 9 and a pharmaceutically acceptable carrier.

18. An antibacterial composition comprising an antibacterial effective amount of the glycopeptide antibiotic of claim 10 and a pharmaceutically acceptable carrier.

19. An antibacterial composition comprising an antibacterial effective amount of the glycopeptide antibiotic of claim 11 and a pharmaceutically acceptable carrier.

20. An antibacterial composition comprising an antibacterial effective amount of the antibiotic of claim 12 and a pharmaceutically acceptable carrier.

21. An animal feed composition comprising a nontoxic amount of the glycopeptide antibiotic complex of claim 1 which is effective in increasing propionate production in the rumen or cecum of a meat or milk producing animal in an animal feed.

22. An animal feed composition comprising a nontoxic amount of the glycopeptide antibiotic of claim 2 which is effective in increasing propionate production in the rumen or cecum of a meat or milk producing animal in an animal feed.

23. An animal feed composition comprising a nontoxic amount of the glycopeptide antibiotic of claim 3 which is effective in increasing propionate production in the rumen or cecum of a meat or milk producing animal in an animal feed.

24. An animal feed composition comprising a nontoxic amount of the glycopeptide antibiotic of claim 4 which is effective in increasing propionate production in the rumen or cecum of a meat or milk producing animal in an animal feed.

25. An animal feed composition comprising a nontoxic amount of the glycopeptide antibiotic of claim 9 which is effective in increasing propionate production in the rumen or cecum of a meat or milk producing animal in an animal feed.

26. An animal feed composition comprising a nontoxic amount of the glycopeptide antibiotic of claim 10 which is effective in increasing propionate production in the rumen or cecum of a meat or milk producing animal in an animal feed.

27. An animal feed composition comprising a nontoxic amount of the glycopeptide antibiotic of claim 11 which is effective in increasing propionate production in the rumen or cecum of a meat or milk producing animal in an animal feed.

28. An animal feed composition comprising a non-toxic amount of the antibiotic of claim 12 which is effective in increasing proprionate production in the rumen or cecum of a meat or milk producing animal in an animal feed.

29. An animal feed premix composition comprising a premix vehicle and from 5-75% by weight of the glycopeptide antibiotic of claim 1.

30. An animal feed premix composition comprising a premix vehicle and from 5-75% by weight of the glycopeptide antibiotic of claim 2.

31. An animal feed premix composition comprising a premix vehicle and from 5-75% by weight of the glycopeptide antibiotic of claim 3.

32. An animal feed premix composition comprising a premix vehicle and from 5-75% by weight of the glycopeptide antibiotic of claim 4.

33. An animal feed premix composition comprising a premix vehicle and from 5-75% by weight of the glycopeptide antibiotic of claim 9.

34. An animal feed premix composition comprising a premix vehicle and from 5-75% by weight of the glycopeptide antibiotic of claim 10.

35. An animal feed premix composition comprising a premix vehicle and from 5-75% by weight of the glycopeptide antibiotic of claim 11.

36. An animal feed premix composition comprising a premix vehicle and from 5-75% by weight of the antibiotic of claim 12.

* * * * *